United States Patent [19]

Gospodarowicz et al.

[11] Patent Number: 4,902,782
[45] Date of Patent: * Feb. 20, 1990

[54] ISOLATION OF FIBROBLAST GROWTH FACTOR

[75] Inventors: Denis Gospodarowicz, San Francisco; Andrew Baird, San Diego, both of Calif.; Peter Bohlen, Uster, Switzerland

[73] Assignee: The Salk Institute for Biological Studies, San Diego, Calif.

[*] Notice: The portion of the term of this patent subsequent to Nov. 15, 2005 has been disclaimed.

[21] Appl. No.: 268,000

[22] Filed: Nov. 7, 1988

Related U.S. Application Data

[63] Continuation of Ser. No. 940,524, Dec. 10, 1986, Pat. No. 4,785,079, and a continuation-in-part of Ser. No. 670,160, Nov. 9, 1984.

[51] Int. Cl.$^4$ ................................................. C07K 3/28
[52] U.S. Cl. ...................................... 530/399; 530/412; 530/413; 530/416; 530/417; 530/418; 530/419; 530/420; 530/422; 530/827; 530/829; 530/837; 530/849
[58] Field of Search ............... 530/399, 412, 413, 416, 530/417-420, 422, 827, 829, 839, 849

[56] References Cited

U.S. PATENT DOCUMENTS 4,444,760 4/1984 Thomas, Jr. ....................... 424/177

OTHER PUBLICATIONS

Thomas et al., *JBC* 255, 1980, pp. 5517-5520.
Gospodarowicz et al., *PNAS* 81(22) 1984, pp. 6973-6977.
Lobb et al., *Biochem.* 23(26) 1984, pp. 6295-6299.
Hau et al., *Chem. Abst.*, vol. 99, 1983, #101835(a).
Tiesner et al., *Chem. Abst.* 98, 1982, #122410(c).
Protein Purification Principles and Practices, ed scopes, 1982, pp. 111-117.
Gospodarowicz, D., et al., *In Vitro 14*, 85-118 (1978).
Gospodarowicz, D., *J. of Biol. Chem.*, 250, 2515-2520 (1975).
Gambarini, A. G., *J. of Biol. Chem.*, 257, 9692-9697 (1982).
Lemmon, S. K. et al., *J. of Cellular Biochemistry*, 21 195-208 (1983).
Gospodarowicz, D. et al., *Nature* 249 123-127 (1974).
Westall, F. C. et al., *Proc. Natl. Acad. Sci. USA* 75, 4756-4678 (1978).
Thomas, K. A. et al., *Proc. Natl. Acad. Sci. USA*, 81 357-361 (1984).
Gospodarowicz, D. et al., *J. of Biol. Chem.*, 257, 12266-12276 (1982).
Gospodarowicz, D. et al., *J. of Biol. Chem.*, 253, 3736-3743 (1978).
Kasper, S. et al., *J. of Biol. Chem.*, 257, 5226-5230 (1982).

Primary Examiner—Garnette D. Draper
Attorney, Agent, or Firm—Fitch, Even, Tabin & Flannery

[57] ABSTRACT

Basic Fibroblast Growth Factor (FGF) is substantially purified by the employment of affinity chromatography using heparin-linked support material. Described is a simplified three step procedure for extracting basic FGF from either mammalian brain or mammalian pituitary tissue. Salt precipitation, e.g., with ammonium sulfate is used to provide a partially purified precipitate that is then subjected to ion-exchange chromatography, e.g., using a Carboxymethyl-Sephadex column. Substantially pure basic FGF fractions are then obtained by fractionating the further partially purified fractions using affinity chromatography on a heparin-linked support e.g., Heparin-Sepharose.

10 Claims, 5 Drawing Sheets

FIG.5A FIG.5B FIG.5C
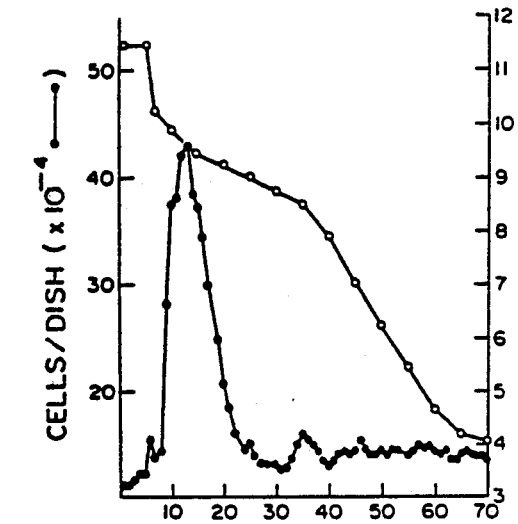
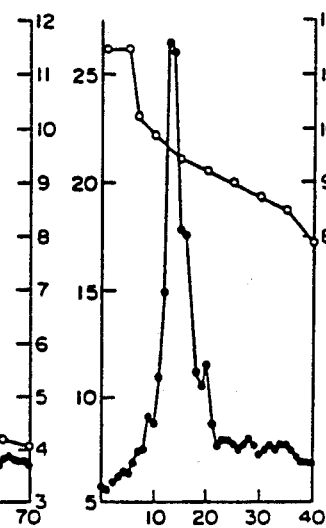
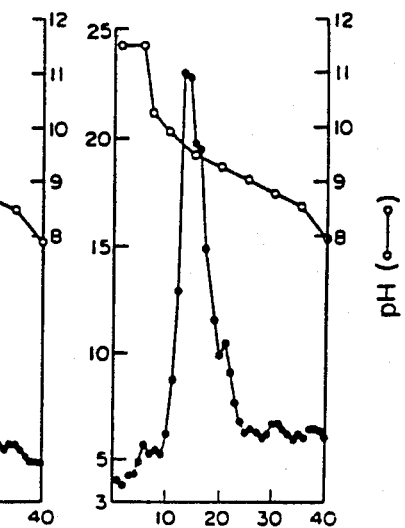
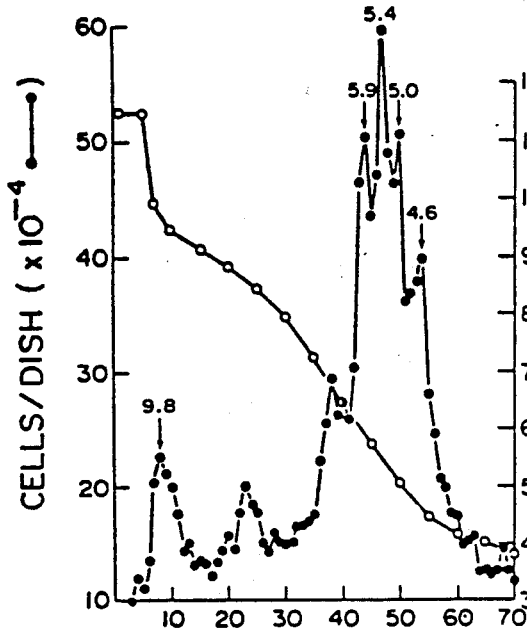
FRACTION NUMBER
FIG.5D FIG.5E FIG.5F

ISOLATION OF FIBROBLAST GROWTH FACTOR

This invention was made with Government support including National Institutes of Health Program Grants No. HD-09690 administered by the National Institute of Child Health and Human Development and No. AM-18811 administered by the National Institute of Arthritis, Diabetes and Digestive and Kidney Diseases. The Government has certain rights in this invention.

This application is a continuation of application Ser. No. 940,524, filed Dec. 10,1986, which is U.S. Pat. No. 4,785,079 a continuation-in-part of our earlier application Ser. No. 670,160 filed Nov. 9, 1984 now abandoned.

The present invention relates to purification of a mammalian protein and more particularly to purification of basic fibroblast growth factor.

BACKGROUND OF THE INVENTION

Both the brain and the pituitary gland have been known to contain mitogenic factors for cultured cells; however, it was unclear what the relationship was with classical pituitary hormones, such as TSH, LH, FSH, GH and ACTH, until the identification in the pituitary gland in 1974 of a growth factor called fibroblast growth factor (FGF). The presence of two forms of FGF, acidic and basic, has now been widely acknowledged by many specialists and research groups working in the fibroblast growth factor area. A thorough description of the events leading to the discovery of the acidic and basic forms of FGF during the period of 1973 to 1978 is contained in *Molecular Cellular Biochemistry*, 25, 79-110 (1979).

The acidic form of FGF was first discovered and identified in 1975, Gospodarowicz, D., *Nature*, 256, 216-219 (1975). At the time of this discovery, Dr. Gospodarowicz was working with myoblasts and accordindly the term myoblast growth factor was used. Purification of an acidic brain GF is also described in U.S. Pat. No. 4,444,760(Apr. 24, 1984).

In 1974, the identification in the pituitary gland of a growth factor called fibroblast growth factor (FGF) was reported which was shown to be distinct from pituitary hormones, Gospodarowicz, D., *Nature*, 249, 123-127 (1974). This growth factor was demonstrated to be a basic protein (pI of 9.6),to be a potent mitogen for either normal diploid fibroblasts or established cell lines, and to have a molecular weight of about 14,000. Subsequent to this discovery, the basic nature of brain and pituitary derived FGFs has been described in further detail in numerous publications, Gospodarowicz et al., J. of Biol. Chem., 253, 3736-3743 (1978); Gospodarowicz et al., *J. of Biol. Chem*, 253, 1226-1276 (1982); Gospodarowicz et al., *J. of Cell. Physiol.*, 122, 323-332 (1985); Lemmon et al., *J. of Cell. Biol.*, 95, 162-169; (1982) Gliwin & Haushcka, *Biochemistry*, 25, 3487-3492 (1986).

Later studies have confirmed that, in addition to fibroblasts, basic FGF is also mitogenic for a wide variety of normal diploid mesoderm-derived and neurocrest-derived cells including granulosa cells, adrenal cortical cells, chondrocytes, myoblasts, corneal and vascular endothelial cells from either bovine or human origin, vascular smooth muscle cells and lens epithelial cells. Basic FGF was also shown to substitute for platelet-derived growth factor in its ability to support the proliferation of fibroblasts exposed to plasma-supplemented medium. Consistent with its ability to stimulate the proliferation of bovine and vascular endothelial cells, basic FGF has a similar activity in vivo on capillary endothelial cells; therefore, basic FGF is also considered an angiogenic factor.

It is this basic form of pituitary and brain FGF with which the applicants' invention is concerned.

Because basic FGF has important value both for promoting cell growth in vitro and as a therapeutic agent, it would be desirable to be able to obtain sizable amounts of substantially pure basic FGF. This is particularly the case where the substance is to be administered to a human, as administration of unseparated impurities in extracts is to be avoided whenever possible.

A need exists for improved, simplified methods of purifying basic FGF.

SUMMARY OF THE INVENTION

Basic brain and pituitary fibroblast growth factors can each be purified to apparent homogeneity from crude tissue extracts by a simplified method which includes a rough pre-purification protocol and an affinity chromatography procedure using a column in which heparin is linked to an insoluble support. Although some proteins have been separated using affinity chromatography with heparin linked to a solid support, only those proteins specifically known to link to heparin have been purified by this technique, and the degree of purity achieved by this technique has been dependent upon what other proteins in the sample similarly exhibited affinity for heparin.

Heparin is a highly sulfated dextrorotary mucopolysaccharide which is a constituent of several mammalian tissues, especially the liver and lungs. Its chief clinical utility is as an anticoagulant. Thus, while heparin would be expected to have specific affinity for certain blood-related proteins and while it would be expected that certain blood proteins could be at least partially purified by affinity chromatography on a column packed with support-linked heparin, the affinity of heparin for other mammalian proteins is random and unpredictable. Very surprisingly, from relative crude preparations of both brain and pituitary tissue, basic fibroblast growth factor is adsorbed by heparin in the affinity chromatography to the virtual exclusion of other brain and pituitary proteins.

A particular three-step embodiment of the method includes in sequence (1) a salt precipitation step, e.g., with ammonium sulfate; (2) a step for the removal of neutral and acid proteins, such as an ion exchange step, e.g., by adsorption to Carboxymethyl-Sephadex, or a metal-chelation step; and (3) heparin-linked affinity chromatography, e.g., Heparin-Sepharose affinity chromatography (HSAC). Such a method can recover substantial amounts of highly purified (greater than 90%) basic FGF in less than 48 hours. Such a method is particularly useful for purifying basic fibroblast growth factor from a variety of organ tissue sources, including brain, pituitary gland, adrenal gland, kidney and placenta. The heparin-linked chromatography may be used without such pre-purification steps when basic FGF is being produced bacterially or in some other cultures, as will be possible using recombinant DNA procedures.

BRIEF DESCRIPTION OF THE DRAWINGS

FIG. 5 is a determination of pI on the basic FGF purified by Heparin-Sepharose.

DETAILED DESCRIPTION OF THE PREFERRED EMBODIMENTS

Figure 1A:
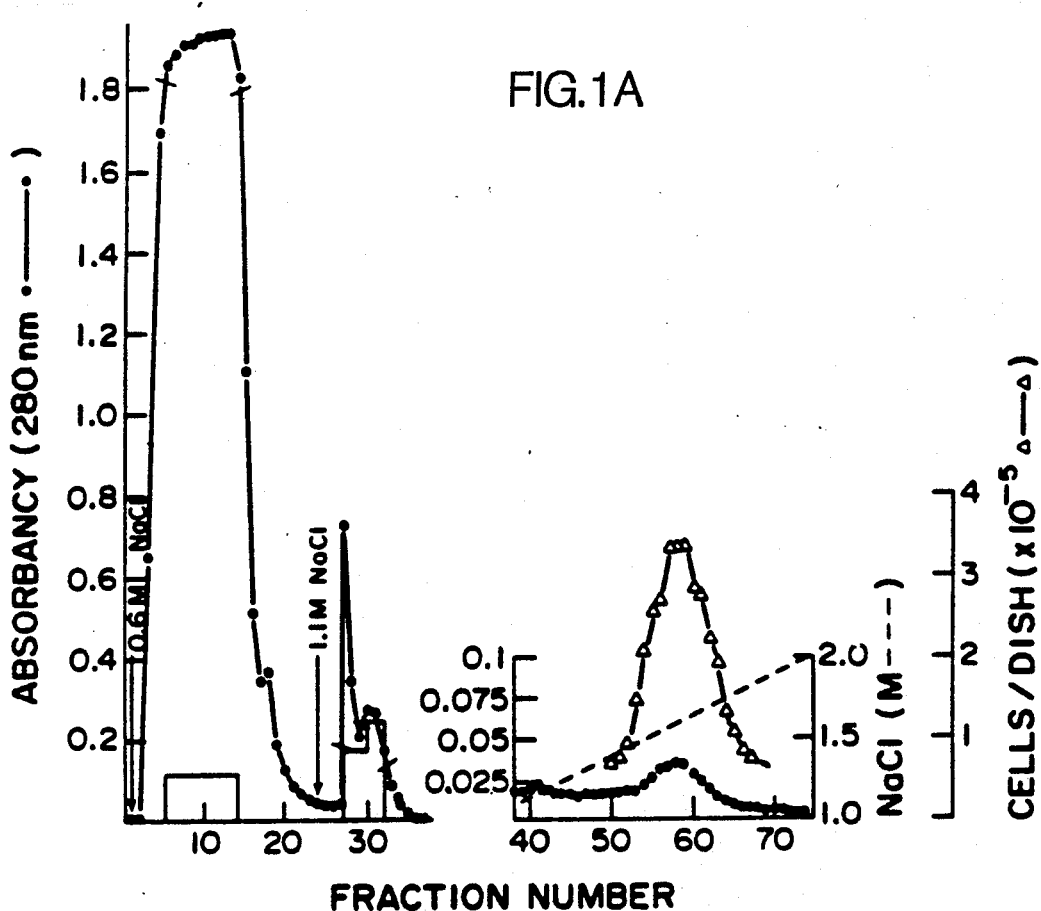
FIG. 1A graphically illustrates results of an experiment in which basic brain FGF is purified according to the present invention. The early eluting basic FGF fractions of the final Heparin-Sepharose chromatography procedure are represented on the left hand side of FIGURE 1A by a measurement of total protein, and the later eluting FGF fractions are represented on the right-hand side by their biological activity.

In accordance with the present invention, a simplified procedure is provided for purifying basic fibroblast growth factor (FGF) from a crude extract. This method achieves a purity heretofore achieved only by more complex separations and recovers a very substantial portion of the basic FGF originally present. The process involves the novel use of affinity chromatography in which heparin is linked to a suitable insoluble support. Surprisingly and unexpectedly, very highly purified basic fibroblast growth factor is obtained from an extract of either brain or pituitary that is only crudely pre-purified. When an extract of soluble components of brain or pituitary tissue is used, it is preferably pre-purified to at least about 0.02-0.05% FGF by weight of total protein. Then a single affinity chromatography procedure using a stationary phase of heparin linked to a solid support purifies the basic fibroblast growth factor over 2400 to 3500 fold to constitute upwards of 90 percent by weight of total protein. When a tissue source is employed, the pre-purification steps could be omitted; however, the expense would be greatly increased as a result of the need to use a far greater quantity of the heparin-linked affinity chromatography material. Likewise one of the two pre-purification steps could be omitted, with a similar increase in overall expense.

In a specific embodiment of the present invention, basic FGF is purified from tissue in a three-step protocol. In the first of three successive steps, a crude extract of either brain or pituitary material is salt-precipitated, e.g., with ammonium sulfate. In a second step, the precipitate is batch-adsorbed upon an ion-exchange resin, such as Carboxymethyl Sephadex. Finally, the active fraction is subjected to affinity chromatography using as the stationary phase support-linked heparin, such as the agarose-linked heparin sold under trademark Heparin-Sepharose. The recovery of either brain or pituitary basic FGF is greater than 90%. The heparin affinity chromatography step alone has been shown to be responsible for 2400- and 3500-fold purification of basic pituitary and brain FGF, respectively, thus constituting an extremely powerful technique. Basic brain and pituitary FGFs purified by heparin affinity chromatography possess the full intrinsic activity of the native molecule whereas the biological potency has previously been very substantially lessened by attempted HPLC-purification.

The invention is described herein with respect to certain materials used as solid supports for chromatography procedures, such as Heparin-Sepharose, and Carboxymethyl Sephadex, which are both effective, to different degrees, for purifying basic FGF and which are commercially available; however, it is to be understood that other solid support material are suitable substitutes as stationary phases. In the affinity chromatography, it is the heparin moieties which have specific affinity for the basic FGF relative to other tissue proteins, and material other than agarose, including but not limited to glass, cellulose, polyacrylamide and cross-linked dextrans, may be used in place of agarose as the solid support to which the heparin moieties are linked. Preferably, a material used as a support should not contain charged or hydrophobic groups, and support particles should be uniform, spherical and rigid.

While the ion-exchange chromatography process is described herein primarily with respect to a cross-linked dextran having functional carboxymethyl moieties and sold, for example, under the trademark Carboxymethyl-Sephadex, other resins, particularly other mildly cationic resins, are suitable for partially purifying basic FGF-containing extracts by ion-exchange chromatography. Other suitable resins include but are not limited to cross-linked dextran having sulphopropyl functional moieties, e.g., that sold under the trademark Sulphopropyl-Sephadex, and polystyrene cross-linked with benzene having sulfate functional moieties.

Generally, a three-step method according to the invention is performed as follows. Frozen brain and pituitary tissues are obtained from J.R. Scientific (Woodland, Calif.), kept in a Revco freezer ($-80°$ C.) and used within a period of two weeks. Solubilized components of the bovine brains (4 kg) or pituitaries (1.8 kg) are extracted, and the extracts are precipitated with 0.15 M ammonium sulfate at pH 4.5, as previously described in Gospodarowicz, D., *Nature* (1974) *supra.*; Gospodarowicz, D., *J. Biol. Chem.* 250, 2515-2520 (1975); and Gospodarowicz, D. et al., *J. Biol. Chem.* 253, 3736-3743 (1978).

Partially purified basic FGF from the ammonium sulfate precipitation is next treated by batch adsorption/elution, using analytical grade Carboxylmethyl-Sephadex C-50 (Pharmacia, Piscataway, N.J.) as described in Gospodarowicz, D. (1975) supra. and Gospodarowics, D. et ap. (1978) supra. The basic FGF-containing fractions are eluted from the ion-exchange column with 0.6 M NaCl/0.1 M sodium phosphate, pH 6.0. The pre-purification should provide a basic FGF-containing fraction in which basic FGF comprises at least 0.02-0.05 percent by weight of total proteins. The partial purification prevents the affinity chromatography material from being overloaded with impure substances and contributes to the final purity of the FGF fraction. Then the partially purified basic FGF is pumped (35 ml/hr.) through a column of analytical grade Heparin-Sepharose (Pharmacia, Piscataway, N.J.) (1.6×5 cm bed, 10 ml volume) that has been equilibrated at room temperature with 10 mM Tris (pH 7.0)/0.6M NaCl. The column is then washed (flow rate 35 ml/hr.) with 10 mM Tris (pH 7.0)/0.6 M NaCl, and further with 10 mM Tris, (pH 7.0)/1.1 M NaCl, until the absorbance of the eluate at 280 nm became negligible. Fractions exhibiting mitogenic activity are then eluted with a linear two-hour salt gradient of 1.1 M to 2 M NaCl in 10 mM Tris, pH 7.0 at 35 ml/hr. Fractions with biological activity are pooled and kept frozen at −80° C.

Various tests are performed to analyze and characterize the basic FGF content of the material obtained from the several purification procedures.

Total protein is determined by the dye fixation assay of Bradford, M., *Anal. Biochem.* 126, 144–150 (1976), using BSA (Schwartz/Mann, Orangeburg, N.J.) as a standard, and/or by amino acid analysis. Amino acid analysis is performed on a Liquimat III analyzer (Kontron, Zurich, Switzerland) that is equipped with an o-phthalaldehyde fluorescence detection system and a proline conversion accessory according to previously described micromethodology of Bohlen, P. & Schroeder, R., *Anal. Biochem.* 126, 144–152 (1982).

During the isolation steps, purification of the growth factor is monitored by testing chromatography fractions for their ability to stimulate the proliferation of adult bovine aortic endothelial (ABAE) cells in culture, as described in Gospodarowicz, D. et al., *J. Biol. Chem.* 257, 12266–12278 (1982); and Gospodarowicz, D. et al., *Proc. Natl. Acad. Sci. USA* 73, 4120–4124 (1976). Briefly, cells are seeded at an initial density of $2 \times 10^4$ cells per 35 mm dish containing 2 ml of DMEM H-16 supplemented with 10% calf serum and antibiotics. Six hours later, a set of triplicate plates is trypsinized, and cells are counted to determine the plating efficiency. Ten $\mu l$ aliquots of the appropriate dilution of each fraction (with DMEM/0.5% BSA) are then added to the dishes every other day. After 4 days in culture, triplicate plates are trypsinized, and final cell densities are determined by counting cells in a Coulter counter. Similar activity can be observed when adrenal cortex capillary endothelial cells instead of ABAE cells are used as target cells.

Aliquots of HSAC-purified FGF are analyzed by reverse-phase HPLC on a Vydac C4 column ($25 \times 0.46$ cm), 5 $\mu m$ particle size, 300 angstrom pore size, using a gradient of acetonitrile in 0.1% (v/v) trifluoroacetic acid (TFA). For performance of sodium dodecyl sulfate (NaDodSO$_4$)-Polyacrylamide gel electrophoresis (PAGE), aliquots (0.5 $\mu g$ protein) from bioactive HSAC fractions are added to a sample buffer composed of 15% (v/v) glycerol, 0.1 M dithiothreitol, 2% (w/v) NaDodSO$_4$, 75 mM Tris-HCl (pH 6.8), 2 mM phenylmethylsulfonylfluoride, 2 mM EDTA, 1 mM N-ethylmaleimide, and 1 mM iodoacetic acid. Samples are boiled for 3 min. and then applied to an exponential gradient (10–18%) polyacrylamide slab gel with a 3% stacking gel, Laemmli, U.K., *Nature* 227, 680–685 (1970); Tauber, J.P. et al., *In Vitro* 17, 519–530 (1981). Electrophoresis is performed for 4 hr. at 20 mA. Gels are stained using the BioRad (Richmond, Calif.) silver nitrate stain kit as described by the manufacturer.

To perform radioimmunoassay (RIA), amino-terminally directed antibodies against basic pituitary FGF are obtained by immunizing three-month old male and female white New Zealand rabbits against the BSA-conjugated synthetic decapeptide Pro-Ala-Leu-Pro-Glu-, Asp-Gly-Gly-Ser-Tyr [Tyr$^{10}$–FGF(1-10)], which represents the amino-terminal sequence of basic pituitary FGF (Bohlen et al., PNAS 81, 5364 (1984)). These antibodies recognize both synthetic antigen and native pituitary fibroblast growth factor on an equimolar basis and are capable of inhibiting the FGF-induced proliferation of vascular endothelial cells in vitro. An RIA is established using the radioiodinated antigen as a tracer and antiserum (716 B4 and B8) at a final dilution of 1 to 5000.

The invention will now be illustrated in greater detail by way of specific examples.

EXAMPLE 1

Bovine brains (in batches of 1 kg) were homogenized in 4 liters of 0.15 M $(NH_4)_2SO_4$. The pH was then adjusted to 4.5 by adding 6 N HCl. The homogenate was stirred in a cold (4° C.) environment for 2 hours, and then centrifuged at $10,000 \times g$, 30 minutes. The pellets were discarded. Supernatants were pooled, neutralized at pH 6.0, and 200 g of $(NH_4)_2SO_4$ per liter was then added. The suspension was stirred for 30 minutes in the cold, and centrifuged at $10,000 \times 30$ minutes. The pellets were discarded, the supernatants were pooled, and 250 g of $(NH_4)_2SO_4$ per liter was added. After stirring (30 min., 4° C.), the suspension was centrifuged ($10,000 \times g$, 30 min.). Supernatants were discarded, and pellets were resuspended in 250 ml of $H_2O$.

The solution was dialyzed overnight to lower the salt concentration below 0.1 M, and was applied the next day on a Carboxymethyl-Sephadex column equilibrated with 0.1 M sodium phosphate, pH 6.0. The breakthrough fraction was discarded; the column was then washed with 0.1 M sodium phosphate, pH 6.0, 0.15 M NaCl, and then was washed with 0.1 M sodium phosphate, pH 6.0, 0.6 M NaCl. The last fraction, which contained most of the mitogenic activity (90%), when tested on low density cultures of vascular endothelial cells, was chromatographed on a Heparin-Sepharose column, as described above. Fractions of 10 ml and 3 ml were collected during sample loading and column washing; fractions of 1.4 ml were collected during gradient elution. Protein concentration in fractions 5 to 14, as graphically illustrated in FIG. 1A, was determined by weighing a 2-ml aliquot after dialysis and lyophilization. For bioassay, aliquots of the pooled fractions 5–14, 28–30 and 31–33 were diluted with Dulbecco's modified Eagle's medium (DMEM)/0.5% bovine serum albumin (BSA), and 10 ul aliquots containing 2 ug, 16 ng and 4 ng, respectively, were added to low density ABAE cell ultures. Bioassay results for these pooled fractions are shown in FIG. 1A in histogram form. Aliquots of fractions 50–67 of the NaCl gradient were diluted 500-fold in DMEM/0.5% BSA, and 10 $\mu l$ aliquots were added to low density ABAE cell cultures. The final cell densities of the cultures after 4 days are shown in FIG. 1A for each fraction (Δ-- Δ). Densities of control cultures after 4 days were $6 \times 10^4$ cells/35 mm dish.

Figure 1B:
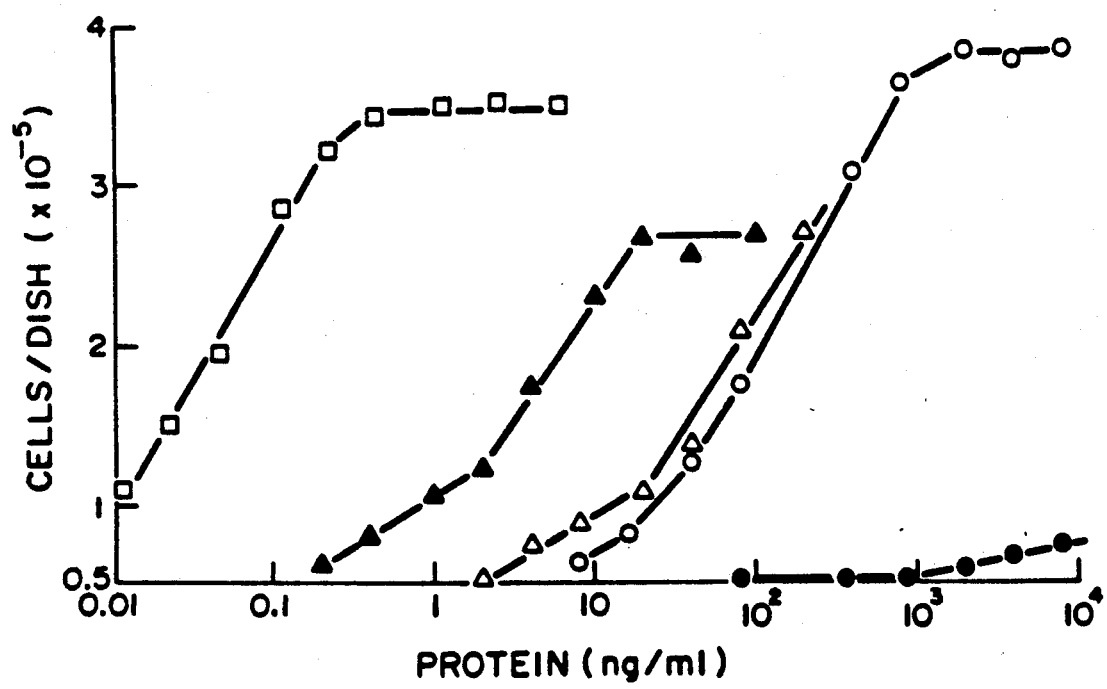
FIGURE 1B graphically illustrates mitogenic activities on adult bovine aortic endothelial ABAE cells of various fractions from the Heparin-Sepharose chromatography procedure as well as the eluate from an intermediate Carboxymethyl-Sephadex chromatography procedure.

Mitogenic activities of fractions from various purification steps were determined on low density ABAE cells. The results as are graphically illustrated in FIG. 1B represent the following fractions: the 0.6 M NaCl Carboxymethyl-Sephadex fraction (o--o), the 0.6 M NaCl HSAC fraction (tubes 5–14, ●--●, the 1.1 M NaCl HSAC fraction (tubes 28–30, Δ--Δ, and (31–33, ▲--▲), and the 1.5 to 1.6 M NaCl HSAC gradient elution fraction (tubes 55–62, □--□)

EXAMPLE 2

Figure 2A:
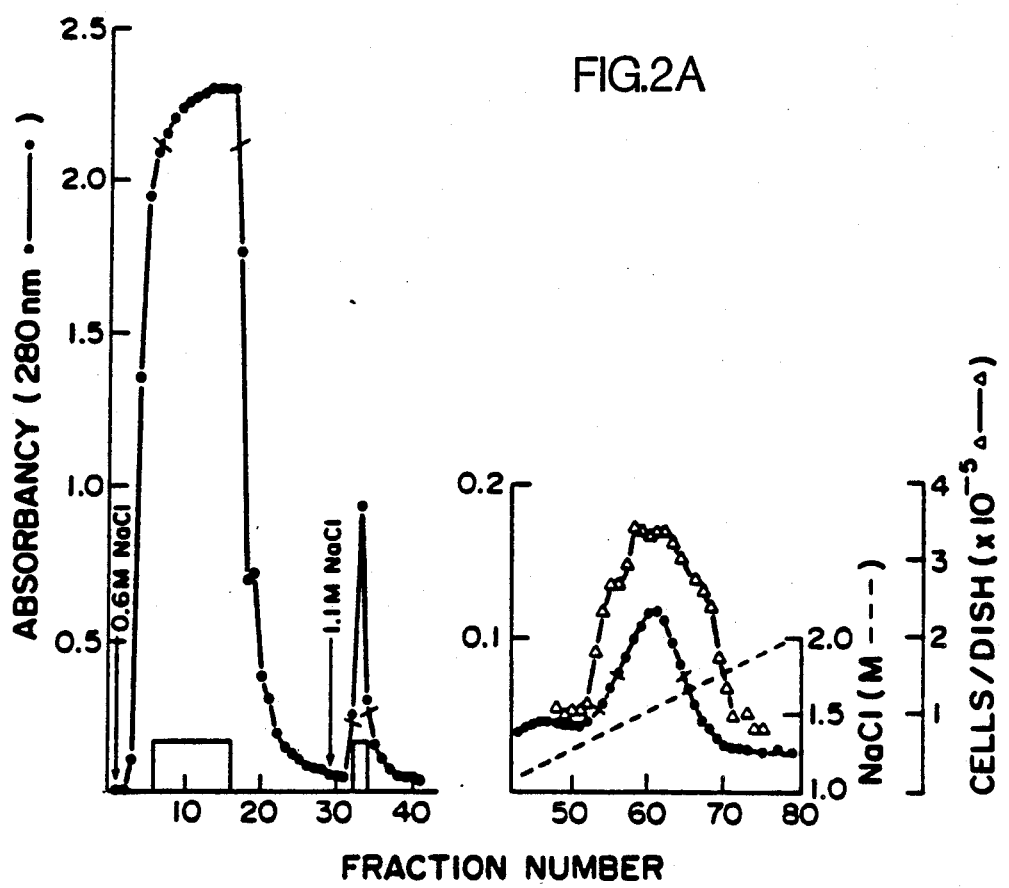
FIG. 2A is similar to FIGURE 1A but gives the result of purification of basic FGF from a pituitary specimen.
Figure 2B:
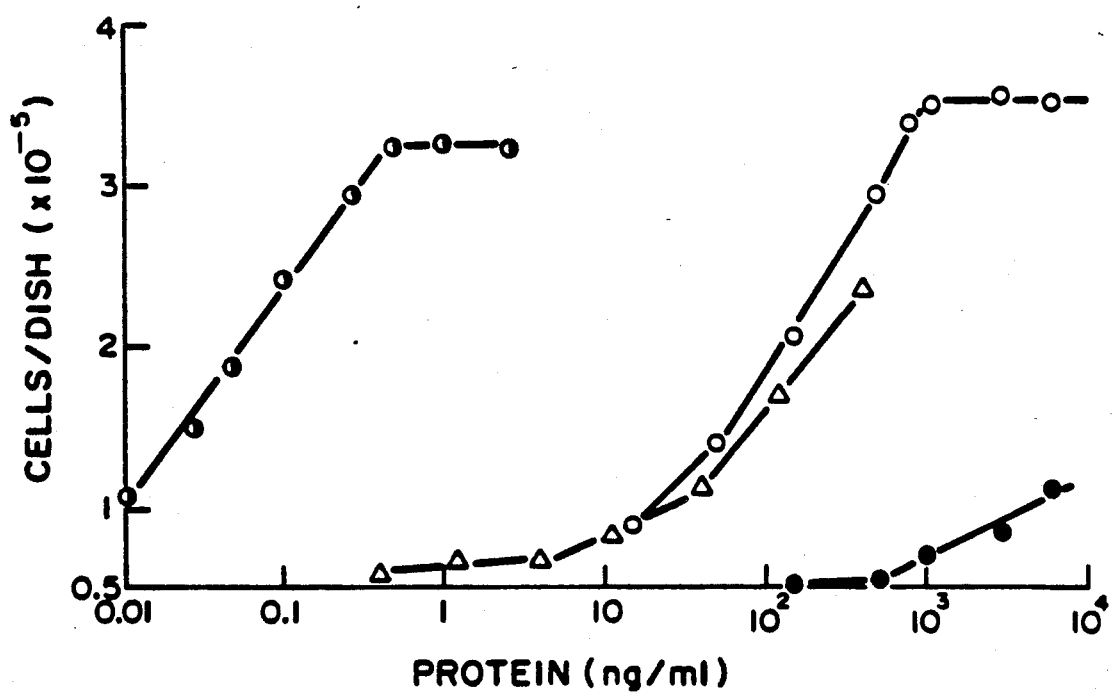
FIG. 2B is similar to FIG. 2A but relates to the pituitary purification.

Basic FGF was partially purified from pituitary tissue by ammonium sulfate precipitation followed by Carboxylmethyl-Sephadex chromatography as described in Example 1 above. The partially purified basic pituitary FGF preparation (0.6 M NaCl Carboxymethyl-Sephadex eluate, 124 ml, 7 mg/ml) was chromatographed on a Heparin-Sepharose column, as described in Example 1. Protein concentrations in fractions 6-15, 33-34 and 54-64 were determined as described in Example 1. Ten µl of the pooled fractions 6-15 and 33-34, containing 2 and 10 ng protein respectively, and fractions 54-64 of the NaCl gradient were assayed as outlined in Example 1, and the results are shown in FIG. 2B.

Mitogenic activities of fractions at various purification steps on low density ABAE cell cultures were determined. Conditions were as in Example 1. Represented in FIG. 2B are: the 0.6 M NaCl Carboxymethyl-Sephadex fraction (o–o), the 0.6 M NaCl HS fraction (tubes 6-15,●–●), the 1.1 M NaCl HS fraction (tubes 33-34, and the 1.5 to 1.6 M NaCl gradient elution fractions (tubes 56-65, o–o.

EXAMPLE 3

Figure 3:
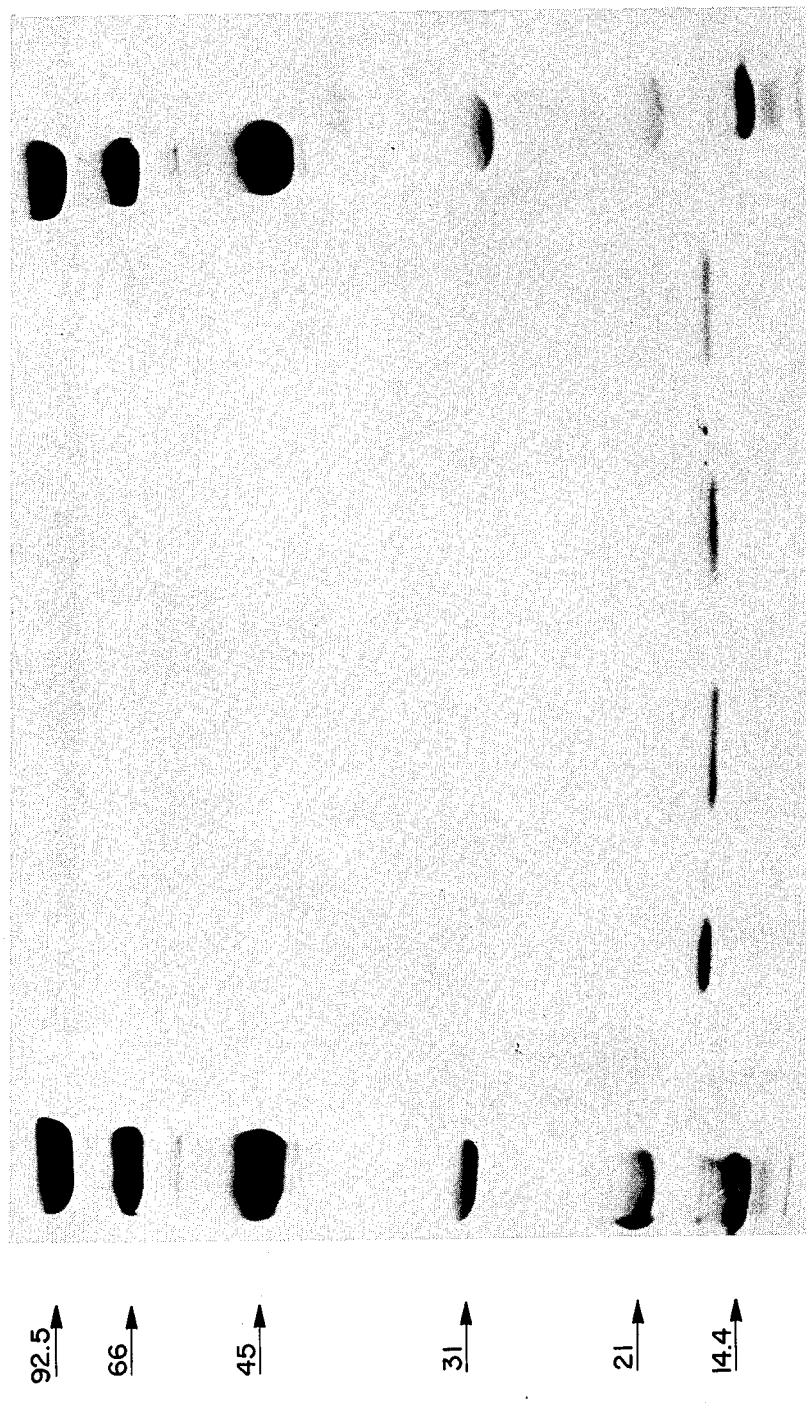
FIG. 3 is an illustration of an electrophoretic pattern obtained by running basic pituitary and brain FGF samples purified by the method of the present invention.

Samples (10 µl, containing 0.5 µg of protein) of heparin-purified brain and pituitary FGF were subjected to NaDodSO4 polyacrylamide gel electrophoresis as described above. Lanes B and D contain HSAC-purified brain FGF; Lane C contains HSAC-purified FGF; Lane E contains basic pituitary FGF purified by FPLC; and Lanes A and F contain a protein standard mixture, including phosphorylase ($M_r$ 31,000), soybean trypsin inhibitor ($M_r$ 21,500) and lysozyme ($M_r$ 14,400). In the migration pattern, shown in FIG. 3, both brain and pituitary FGF migrated as single bands with apparent molecular weights of 16,000. Similar migration patterns were observed regardless of whether or not the samples were run under reducing conditions.

EXAMPLE 4

Figures 4A, 4B:
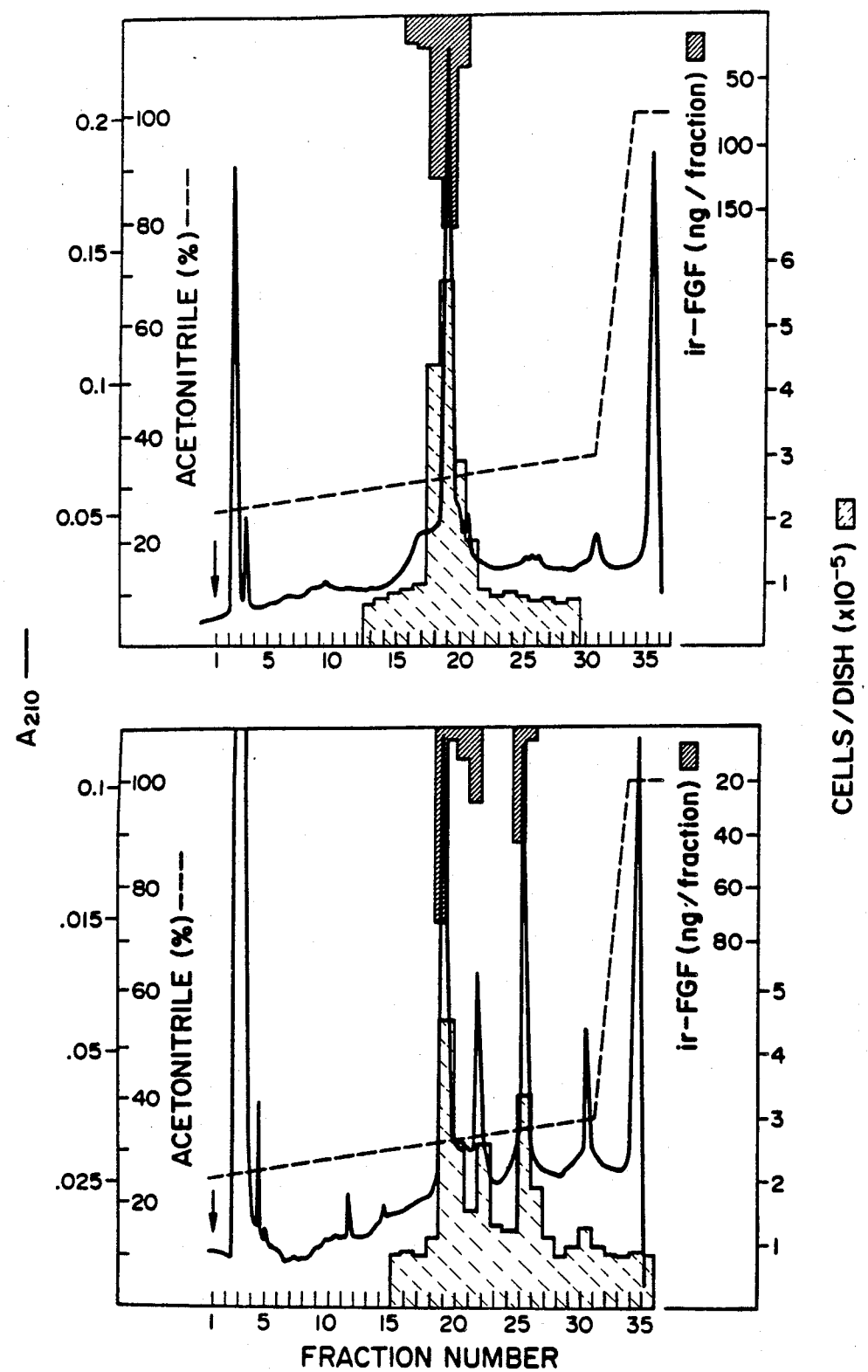
FIG. 4A is a graphic illustration of fractions obtained by further subjecting basic pituitary FGF, which was purified by the method of the present invention, on an HPLC column.
FIG. 4B is a graphic illustration, similar to FIG. 4A, but showing the results with purified basic brain FGF.

Reverse phase HPLC of heparin-purified basic pituitary FGF was performed. Pituitary FGF: 80 µl (20 µg protein) of the pooled fractions 56 to 62 (FIG. 2A) was diluted with 930 µl of 0.2 M acetic acid, and 1 ml was injected into a $C_4$ column equilibrated in 0.1% (v/v) trifluoroacetic acid (TFA). Protein was eluted with a linear 90-min. acetonitrile gradient in 0.1% TFA (25% to 36% (v/v) acetonitrile). Flow rate was 0.6 ml/min, and fractions of 1.8 ml were collected. Aliquots were bioassayed as described above. 20 µl aliquots were subjected to RIA. The results are illustrated in FIG. 4A. Absorbance peaks corresponding to fractions 2-3 and fractions 34-35 did not contain significant amounts of protein, as determined by amino acid analysis. The migratory behavior of HSAC-purified brain and pituitary FGF on reverse-phase HPLC was identical to that of homogenous pituitary FGF which had been isolated using HPLC.

Basic pituitary FGF is shown by reverse phase HPLC to be highly pure, as judged by the presence of only minor impurities eluting before and after the biologically active UV-absorbing peak (FIG. 4A). The impurities amount to less than 10% of the material eluting in the main peak. In contrast, the elution profile of HSAC-purified basic brain FGF shows four distinct peaks (FIG. 4B), the largest (fraction 19) having a retention time identical to that of basic pituitary FGF. The three additional peaks (fractions 22, 25 and 30) do not represent unrelated impurities, because they possess biological activity. Furthermore, basic pituitary FGF and all forms of basic brain FGF are immunoreactive when assayed in a RIA using amino-terminally directed antibodies against pituitary FGF (FIGS. 4A and 4B).

Exposure of HSAC-purified basic FGF to acidic conditions of reverse-phase HPLC results in drastic reduction (95%) of biological potency. This inactivation is very similar to that found previously for basic pituitary FGF purified by HPLC. (Bohlen et al., PNAS 81, 5364 (1984)).

The degree of purification of basic FGF is summarized in Table 1 below. The crude extract represents the salt-precipitated protein extract and the purifications achieved by the subsequent two steps are related thereto.

EXAMPLE 5

(See FIG. 5, A–C.) Heparin-Sepharose affinity purified basic pituitary FGF (100 µg) was dialyzed against 0.1 M NF4 carbonate overnight, lyophilized and redissolved together with 1 mg of an inactive side fraction in 2 ml. gradient solution. This sample was mixed in the midposition of a sucrose density gradient (5–50% w/v) using 1 ml of LKB ampholytes pH 3 to 10 and 3 ml of pH 9 to 11. Isoelectric focusing was performed using a 110 ml LKB column (11, 15). The separation was carried out at 40° C. for 48 hr. at 1000 v. The gradient was then collected in 1.4 ml fractions. The pH of every fifth tube was determined (o) and aliquots of each fraction diluted to 1 to 1000 in DMEM, 0.5% BSA before being tested for their ability to stimulate (o) the proliferation of bovine brain-derived capillary endothelial (A), bovine adrenal cortex cells (B), and human umbilical endothelial cells (C). This basic brain FGF sharply focused with a pI of 9.6.

(See FIG. 5, D–F.) Heparin-Sepharose affinity purified acidic FGF (1 mg) was dialyzed and lyophilized as described above. It was then mixed in the mid position of a sucrose density gradient (5–50% w/v) using 2 ml of LKB ampholytes pH 3 to 10 and 2 ml of pH 9 to 11. Isoelectric focusing was performed as described above. Aliquots of each fraction diluted to 1 to 50 in DMEM 10.5% BSA were tested for their ability to stimulate the proliferation of bovine brain-derived capillary endothelial cells (D), bovine adrenel cortex cells (E), and human umbilical endothelial cells (F). This acidic FGF generated 3 incompletely resolved bio-active peaks with pI of 6.0 –5.9, 5.4 and 5.0 to 4.8.

TABLE 1

| | PURIFICATION OF BASIC BRAIN AND PITUITARY FGF | | | | | |
|---|---|---|---|---|---|---|
| Purification Step | Protein Recovered (mg) | Maximal mitogenic effect (ng/ml) | $ED_{50}$* (ng/ml) | Total activity (units** × $10^5$) | Recovery of Biological activity % | Purification Factor |
| BRAIN: | | | | | | |
| Crude Extract | 15,000 | 150 × $10^3$ | 14 × $10^3$ | 10.7 | 100 | 1 |
| Carboxymethyl-Sephadex C-50 | 180 | 2 × $10^3$ | 210 | 8.6 | 80 | 66 |
| Heparin-Sepharose | 0.033 | 0.4 | 0.04 | 8.3 | 77 | 350,000 |
| PITUITARY: | | | | | | |

TABLE 1-continued

PURIFICATION OF BASIC BRAIN AND PITUITARY FGF

| Purification Step | Protein Recovered (mg) | Maximal mitogenic effect (ng/ml) | ED$_{50}$* (ng/ml) | Total activity (units** × 10$^5$) | Recovery of Biological activity % | Purification Factor |
|---|---|---|---|---|---|---|
| Crude Extract | 26,000 | 75 × 10$^3$ | 7 × 10$^3$ | 37.1 | 100 | 1 |
| Carboxymethyl Sephadex C-50 | 450 | 1.5 × 10$^3$ | 120 | 37.5 | 101 | 58 |
| Heparin-Sepharose | 0.150 | 0.4 | 0.05 | 30.0 | 81 | 140,000 |

*defined as the concentration of the FGF preparation required to give a 50% maximal response in the assay system.
**one unit of activity is defined as the quantity of FGF required to give half-maximal stimulation of cell proliferation in the assay system described.

The data supports the conclusion that the purification of both brain and pituitary basic FGF is as good as that obtained by previously-described, more complex method, i.e., greater than 90% based on weight of total protein. Furthermore, the percentage of basic FGF initially present in the precipitated protein is very high, i.e., upward of 75%. An important advantage of the method is its simplicity relative to other methods. In particular, the method avoids the need for HPLC techniques which are more complex and relatively time-consuming. Only three purification steps are required to obtain substantially pure basic FGF, in contrast to the multi-steps required in certain procedures heretofore described.

The purification of basic FGF according to the simplified method taught herein has led to several important conclusions regarding the nature of basic FGF. The amino acid compositions of HSAC-purified brain and pituitary basic FGFs are strikingly similar, as shown in Table 2 below, and are very close to that of basic pituitary FGF isolated by HPLC. It is now known that the amino-terminal sequence of bovine brain FGF (the major peak, FIG. 4b) is identical to that of bovine pituitary FGF. This constitutes additional evidence for the purity of heparin-purified FGF from both pituitary and brain. Interestingly, the amino acid compositions of the three forms of brain FGF as seen by HPLC are all similar, suggesting that the various forms of brain FGF may be structurally related.

TABLE 2

AMINO ACID COMPOSITION OF BASIC BRAIN AND PITUITARY FGF[a]

| | HSAC-purified Brain FGF[b] | HSAC-purified Pit. FGF[b] | Pit. FGF[c] |
|---|---|---|---|
| Asx | 11.5 | 11.2 | 10[c] |
| Thr | 4.4 | 4.4 | 4 |
| Ser | 8.9 | 8.8 | 9 |
| Glx | 11.3 | 12.9 | 12 |
| Gly | 16.1 | 15.3 | 16 |
| Ala | 9.3 | 9.0 | 9 |
| Val | 5.2 | 5.6 | 5 |
| Met | 2.1 | 2.3 | 2 |
| Ile | 3.0 | 3.3 | 3 |
| Leu | 12.1 | 12.1 | 11 |
| Tyr | 5.8 | 5.9 | 7 |
| Phe | 7.2 | 6.5 | 7 |
| His | 1.8 | 2.3 | 3 |
| Trp | 1.0 | 1.0 | 1 |
| Lys | 14.2 | 14.0 | 13 |
| Arg | 10.3 | 10.0 | 11 |
| Cys | 4.6 | 4.0 | 6 |
| Pro | 9.2 | 9.3 | 9 |

[a]Values represent residues/molecule determined from 24 hr. hydrolysates (with 5.7 M HCl) of 10-30 pmol protein and are not corrected for hydrolysis losses. Procedures for obtaining values for all amino acids are described in Bohlen et al., Anal. Biochem. 126, 144-152 (1982). Compositions are calculated for a 138 amino acid protein which is in agreement with the observed molecular weight.
[b]Values are means of duplicate determinations.
[c]Amino acid composition of pituitary FGF purified with HPLC.

The combined data (molecular weight, HPLC retention time, amino acid composition, amino-terminal sequence, immuno- and bio-activity) suggest that basic pituitary FGF and the major form of basic brain FGF are structurally very similar, possibly even identical. This conclusion is further supported by preliminary finding that HSAC-purified brain and pituitary basic FGFs are also indistinguishable with respect to their immunoreactivity with murine IgM monoclonal antibodies raised against homogeneous pituitary basic FGF prepared by HPLC.

Basic brain FGF consists of multiple molecular forms which appear to be structurally related, based upon their close similarities with respect to immuno and bio-reactivities and on their amino acid compositions and molecular weights. Because all forms are recognized by specific antisera raised against a synthetic replicate of the amino-terminal sequence of pituitary FGF, it is likely that all forms of brain FGF share the same amino-terminal sequence already determined for pituitary FGF, Pro-Ala-Leu-Pro-Asp-Gly-Gly-Ser, or a sequence very similar. The nature of the structural differences between the various forms of brain FGF is not yet clear, and it is likely that they are reflections of protein side chain modifications or microheterogeneity of FGF.

Brain and pituitary FGF preparations, as reported earlier, are mitogenic for a wide variety of normal diploid cultured cells derived from tissue originating from the primary or secondary mesenchyme, as well as from neuroectoderm. These include rabbit chondrocytes, bovine granulosa and adrenal cortex cells, bovine corneal endothelial cells, capillaries endothelial cells derived from bovine adrenal cortex and human umbilical endothelial cells. HSAC-purified brain and pituitary basic FGFs have identical spectra of activity. Moreover, Heparin-Sepharose affinity purified brain and pituitary basic FGF are potent angiogenic factors in vivo. Slow-release forms of brain or pituitary basic FGF containing 1 μg of the growth factor were capable of eliciting a maximal angiogenic response when implanted in either the hamster cheek pouch or in the chick chorioallantoic membrane.

Acidic and neutral forms of FGF have been reported to be present in acidic (pH 4.5) pituitary and brain extracts, Thomas, K. A. et al., J. Biol. Chem. 255, 5517-5520 (1980); Lemmon, S. K. et al., J. Cell. Biochem. 95, 162-169 1982; and Gambarini, A.G. & Armelin, H. A., J. Biol. Chem. 257, 9692-9697 (1982). Our studies find that more than 99% of the bio-activity of pituitary and brain extracts so subjected to heparin affinity chromatography is strongly bound by Heparin-Sepharose. The high recovery of FGF (80-83%) in the 1.5-1.6 M NaCl fractions and the presence of only small amounts of bio-activity in side fractions from the ammonium sulfate and Carboxymethyl-Sephadex steps, Gospodarowicz, D., *J. Biol. Chem.* (1975) supra; Gospodarowicz, D., et al. (1978) supra; and Gospodarowicz et al. (1982) supra, indicate that FGF is the major form of mitogen present in acidic extracts of brain and pituitary tissue. This is in contrast with earlier reports, e.g., Thomas, K. A. et al. (1980) supra, and Gambarini, A.G. et al. (1982) supra, claiming that significant amounts of acidic FGF can be present in partially purified preparations of brain or pituitary extracted at pH 4.5. It is also in contrast with a recent report, i.e., Thomas, K. A., et al., *Proc. Natl. Acad. Sci. USA* 81, 357-361 (1984), describing the purification to homogeneity of an anionic form of FGF from acidic (pH 4.5) brain extracts Apparently, multiple forms of FGF are present in brain which are biologically, but not necessarily structurally, related. The isolation of basic or acidic FGF as the major mitogenic form may depend on minor differences in the isolation protocols or assays used.

The data accumulated herein establishes the virtual identity of basic brain and pituitary FGF. Because pituitary FGF has seen partially characterized structurally and has been shown to be unlike any myelin basic protein fragments, the previous identification of brain FGF as degradation products of MBP, see Westall, F.C., et al., *Proc. Natl. Acad. Sci. USA* 75, 4675-4678 (1978), must be considered erroneous. It is likely that, as suggested by others, e.g., Thomas, K. A.., et al. (1980) supra, brain FGF was co-purified with MBP fragments when brain extracts were processed through the purification scheme previously described by Gospodarowicz, D. et al. (1978), supra.

While the invention has been described in terms of certain preferred embodiments, modifications obvious to one with ordinary skill in the art may be made without departing from the scope of the present invention. For example, although the invention has been described primarily in terms of isolation of basic FGF from brain and pituitary tissues, the method is applicable to isolation of basic FGF from other tissues which contain substantial amounts of the mitogen. In particular, basic FGF may be isolated from kidney, adrenal gland and placenta tissue. Human placenta tissue represents perhaps the only tissue that is generally available for the isolation of human FGF.

Various features of the invention are set forth in the following claims.

What is claimed is:

1. A method for separating basic fibroblast growth factor (bFGF) from a biological sample, said method comprising the steps of: binding bFGF in the biological sample to heparin linked to an insoluble support; eluting bFGF from said linked heparin by gradient fractionation; and selecting for fractions capable of inducing proliferation of vascular endothelial cells in vitro.

2. A method according to claim 1 wherein the eluted bFGF exhibits an increased purity of at least about 2400 to 3500 fold, compared to the biological sample.

3. A method according to claim 1, wherein the eluted bFGF comprises at least about 90 percent by weight of protein in the eluent from the gradient fractionation.

4. A method according to claim 1, wherein the biological sample is pre-purified to contain at least about 0.02 to 0.05 percent bFGF by weight of total protein.

5. A method according to claim 4, wherein the pre-purification includes a salt precipitation step.

6. A method according to claim 5, wherein the salt is ammonium sulfate, at a concentration of about 0.15M.

7. A method according to claim 5, wherein the pe-purification includes a step for removal of neutral or acidic proteins in the biological sample.

8. A method according to claim 7, wherein the removal step utilizes an ion exchange resin.

9. A method according to claim 4, wherein the biological sample is an organ tissue selected from the group consisting essentially of brain, pituitary gland, adrenal gland, kidney and placenta.

10. A method according to claim 1, wherein the gradient fractionation utilizes a NaCl salt gradient of 1.1 M to 2 M.

* * * * *

UNITED STATES PATENT AND TRADEMARK OFFICE
CERTIFICATE OF CORRECTION

PATENT NO. :   4,902,782

DATED      :   February 20, 1990

INVENTOR(S) :  Gospodarowicz, et al.

It is certified that error appears in the above-identified patent and that said Letters Patent is hereby corrected as shown below:

Column 1, Line 40:  Change "GF" to --FGF--.

Column 6, Line 47:  Change "ultures" to --cultures--.

Column 6, Line 60:  Between "●--●" and ",", insert --)--. (close parenthesis).

Column 6, Line 61:  Between " Δ -- Δ ", and ",", insert --)-- (close parenthesis).

Column 7, Line 17:  After "●--●", insert --)--. (close parenthesis).

Column 7, Line 18:  After "33-34," insert -- Δ -- Δ ),--.

Column 7, Line 19:  Between "o--o" and the period, insert --)--. (close parenthesis).

Column 10, Line 27: Change "immunoand" to --immuno- and--.

Column 11, Line 21: Change "seen" to --been--.

Signed and Sealed this

Third Day of September, 1991

Attest:

HARRY F. MANBECK, JR.

Attesting Officer         Commissioner of Patents and Trademarks